US00PP20067P2

(12) United States Plant Patent
Engel

(10) Patent No.: US PP20,067 P2
(45) Date of Patent: Jun. 9, 2009

(54) ***ARGYRANTHEMUM* PLANT NAMED 'SY TAG 5006'**

(50) Latin Name: *Argyranthemum frutescens*
Varietal Denomination: SY TAG 5006

(75) Inventor: Frauke Engel, Havixbeck (DE)

(73) Assignee: Amerinova Properties LLC, Bonsall, CA (US)

( * ) Notice: Subject to any disclaimer, the term of this patent is extended or adjusted under 35 U.S.C. 154(b) by 0 days.

(21) Appl. No.: 12/154,224

(22) Filed: May 21, 2008

(51) Int. Cl.
*A01H 5/00* (2006.01)

(52) U.S. Cl. ..... Plt./406
(58) Field of Classification Search ..... Plt./406
See application file for complete search history.

*Primary Examiner*—Annette H Para
(74) *Attorney, Agent, or Firm*—C. A. Whealy

(57) ABSTRACT

A new and distinct cultivar of *Argyranthemum* plant named 'SY TAG 5006', characterized by its compact, upright to slightly outwardly spreading and mounded plant habit; freely branching growth habit; freely flowering habit; single-type inflorescences with ray florets that are initially light pink in color becoming red purple with development; and good garden performance.

1 Drawing Sheet

Botanical designation: *Argyranthemum frutescens.*
Cultivar denomination: 'SY TAG 5006'.

BACKGROUND OF THE INVENTION

The present invention relates to a new and distinct cultivar of *Argyranthemum* plant, botanically known as *Argyranthemum frutescens* and hereinafter referred to by the name 'SY TAG 5006'.

The new *Argyranthemum* is a product of a planned breeding program conducted by the Inventor in Billerbeck/Beerlage, Germany. The objective of the breeding program is to create new compact and freely branching and flowering *Argyranthemum* cultivars with unique and attractive ray floret coloration.

The new *Argyranthemum* originated from an open-pollination in 2004 in Billerbeck/Beerlage, Germany of the *Argyranthemum frutescens* cultivar SY 01 04, not patented, as the female, or seed, parent with an unknown selection of *Argyranthemum frutescens,* as the male, or pollen, parent. The new *Argyranthemum* was discovered and selected by the Inventor as a single flowering plant within the progeny of the stated open-pollination in a controlled greenhouse environment in Billerbeck/Beerlage, Germany in 2005.

Asexual reproduction of the new *Argyranthemum* by vegetative cuttings in a controlled greenhouse environment in Bonsall, Calif. since December, 2006 has shown that the unique features of this new *Argyranthemum* are stable and reproduced true to type in successive generations.

SUMMARY OF THE INVENTION

Plants of the new *Argyranthemun* have not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'SY TAG 5006'. These characteristics in combination distinguish 'SY TAG 5006' as a new and distinct cultivar of *Argyranthemum:*

1. Compact, upright to slightly outwardly spreading and mounded plant habit.
2. Freely branching growth habit; dense and bushy habit.
3. Freely flowering habit.
4. Single-type inflorescences with ray florets that are initially light pink in color becoming red purple with development.
5. Good garden performance.

Plants of the new *Argyranthemum* differ from plants of the female parent, 'SY 01 04' in the following characteristics:

1. Plants of the new *Argyranthemum* are more compact than plants of 'SY 01 04'.
2. Plants of the new *Argyranthemum* are more freely branching and bushier than plants of 'SY 01 04'.
3. Ray florets of plants of the new *Argyranthemum* are initially light pink in color becoming red purple with development whereas ray florets of plants of 'SY 01 04' are pink in color.

Plants of the new *Argyranthemum* can be compared to plants of the *Argyranthemum* 'M9/18D', disclosed in U.S. Plant Pat. No. 14,470. In side-by-side comparisons conducted in Bonsall, Calif. plants of the new *Argyranthemun* differed from plants of 'M9/18D' in the following characteristics:

1. Plants of the new *Argyranthemum* were more compact than and not as open as plants of 'M9/18D'.
2. Plants of the new *Argyranthemum* were more freely branching than plants of 'M9/18D'.

BRIEF DESCRIPTION OF THE PHOTOGRAPHS

The accompanying photographs illustrate the overall appearance of the new *Argyranthemum.* These photographs show the colors as true as it is reasonably possible to obtain in colored reproductions of this type. Colors in the photographs may differ slightly from the color values cited in the detailed botanical description which accurately describe the colors of the new *Argyranthemum*.

The photograph at the bottom of the sheet comprises a side perspective view of a typical flowering plant of 'SY TAG 5006' grown in a container.

The photograph at the top of the sheet is a close-up view of typical inflorescences of 'SY TAG 5006'.

DETAILED BOTANICAL DESCRIPTION

The aforementioned photographs and following observations and measurements describe plants grown in a polyethylene-covered greenhouse during the late winter/early spring in Bonsall, Calif. and under conditions and practices which approximate those generally used in commercial *Argyranthemum* production. During the production of the plants, day temperatures averaged 27° C. and night temperatures averaged 20° C. Rooted young plants were planted in 15-cm containers and had been growing for six weeks when the photographs and description were taken. In the following description, color references are made to The Royal Horticultural Society Colour Chart, 2001 Edition, except where general terms of ordinary dictionary significance are used.

Botanical classification: *Argyranthemum frutescens* 'SY TAG 5006'.

Parentage:

*Female, or seed, parent.*—*Argyranthemum frutescens*, 'SY 01 04', not patented.

*Male, or pollen, parent.*—Unknown selection of *Argyranthemum frutescens* not patented.

Propagation:

*Type.*—Vegetative cuttings.

*Time to initiate roots, summer.*—About 10 days at temperatures of 25° C.

*Time to initiate roots, winter.*—About 15 days at temperatures of 20° C.

*Time to produce a rooted young plants, summer.*—About 15 days at temperatures of 25° C.

*Time to produce a rooted young plants, winter.*—About 20 days at temperatures of 20° C.

*Root description.*—Fibrous, medium thickness, white in color.

*Rooting habit.*—Moderate branching; moderately dense.

Plant description:

*Appearance.*—Herbaceous single-type potted *Argyranthemum*. Compact, upright to slightly outwardly spreading and mounded plant habit. Strong and freely branching growth habit with about 12 to 15 lateral branches developing per plant each with numerous secondary branches; dense and bushy habit. Vigorous growth habit.

*Plant height.*—About 30 cm.

*Plant width.*—About 21 cm.

*Lateral branches.*—Length: About 28 cm. Diameter: About 3.5 mm. Internode length: About 1 cm to 1.2 cm. Strength: Strong. Texture: Smooth, glabrous. Color: Close to 146C.

Foliage description:

*Arrangement.*—Alternate, simple.

*Length.*—About 4 cm.

*Width.*—About 3.7 cm.

*Shape.*—Deeply dissected with three to five irregular lobes.

*Apex.*—Acute.

*Base.*—Oblique.

*Margin.*—Deeply incised.

*Texture, upper and lower surfaces.*—Smooth, glabrous.

*Venation pattern.*—Pinnate.

*Color.*—Developing foliage, upper and lower surfaces: Close to 146A. Fully expanded foliage, upper surface: Close to N137D; venation, close to 137B. Fully expanded foliage, lower surface. Close to 137C; venation, close to 137C.

*Petiole length.*—About 4.2 cm.

*Petiole diameter.*—About 4 mm.

*Petiole texture, upper and lower surfaces.*—Smooth, glabrous.

*Petiole color, upper surface.*—Close to 137B.

*Petiole color, lower surface.*—Close to 137C.

Inflorescence description:

*Appearance.*—Single-type inflorescence form with ligulate-shaped ray florets. Inflorescences borne on terminal and axillary peduncles above foliage. Disc and ray florets arranged acropetally on a capitulum.

*Fragrance.*—None detected.

*Flowering season.*—Plants flower from spring to fall in Southern California, flowering continuous during this period.

*Inflorescence longevity.*—Inflorescences last about seven to ten days on the plant; inflorescences persistent.

*Quantity of inflorescences.*—Freely flowering, about 68 inflorescences develop per plant.

*Inflorescence bud.*—Height: About 1 cm. Diameter: About 8 mm. Shape: Ovoid. Color: Close to 155C.

*Inflorescence size.*—Diameter: About 3.4 cm. Depth (height): About 1.1 cm. Diameter of disc: About 1.2 cm. Receptacle height: About 5 mm. Receptacle diameter: About 1.2 cm. Receptacle color: Close to 146B.

*Ray florets.*—Shape: Ligulate. Orientation: Initially upright, then perpendicular to the peduncle; apices reflexing with development. Length: About 1.5 cm. Width: About 4 mm. Apex: Emarginate. Base: Acute. Margin: Entire. Texture, upper and lower surfaces: Smooth, glabrous; longitudinally ridged. Number of ray florets per inflorescence: About 20 arranged in one to two whorls. Color: When opening, upper surface: Ground color, close to N155D; with development, tinted with close to 64B to 64D. When opening, lower surface: Ground color, close to N155D; towards the apex, tinted with close to 64B. Fully opened, upper surface: Close to 61A; at the base, N155D. With development, color shifts/fades to close to N77B. Fully opened, lower surface: Close to 186C to 186D.

*Disc florets.*—Arrangement: Massed at center of receptacle. Shape: Tubular, elongated. Apex: Five-pointed. Length: About 6 mm. Width: About 1.5 mm. Number of disc florets per inflorescence: About 128. Color, immature: Apex: Close to 151B. Mid-section: Close to 15A. Base: Close to 145B. Color, mature: Apex: Close to 3A. Mid-section: Close to 145D. Base: Close to 157C.

*Phyllaries.*—Number of phyllaries per inflorescence: About 32 in three whorls. Length: About 3 mm. Width: About 1 mm. Shape: Elliptical. Apex: Acute. Base: Truncate. Margin: Entire. Texture, upper surface: Smooth, glabrous. Texture, lower surface: Scattered pubescence. Color, upper surface: Close to 145A to 145B. Color, lower surface: Close to 146B.

*Peduncles.*—Length, terminal peduncle: About 6 cm. Length, fourth peduncle: About 3.7 cm. Diameter: About 1 mm. Angle: Erect to about 45° from vertical. Strength: Moderately strong, flexible. Texture: Smooth, glabrous; longitudinally ridged. Color: Close to 146B.

*Reproductive organs.*—Androecium: Quantity per disc floret: Five. Filament length: About 1 mm. Filament color: Close to 145D. Anther shape: Oblong. Anther length: About 1.5 mm. Anther color: Close to 7A. Pollen amount: Scarce. Pollen color: Close to 13A. Gynoecium (present on ray and disc florets): Pistil length: About 5 mm. Stigma shape: Two-parted. Stigma color: Close to 151C. Style length: About 2 mm. Style color: Close to 150C. Ovary color: Close to 157D.

*Seed/fruit.*—Seed and fruit production has not been observed.

Disease/pest resistance: Resistance to pathogens and pests common to *Argyranthemums* has not been observed on plants grown under commercial conditions.

Garden performance: Plants of the new *Argyranthemum* have been observed to have good garden performance and to tolerate wind, rain and temperatures from about 1° C. to about 40° C.

It is claimed:

1. A new and distinct *Argyranthemum* plant named 'SY TAG 5006' as illustrated and described.

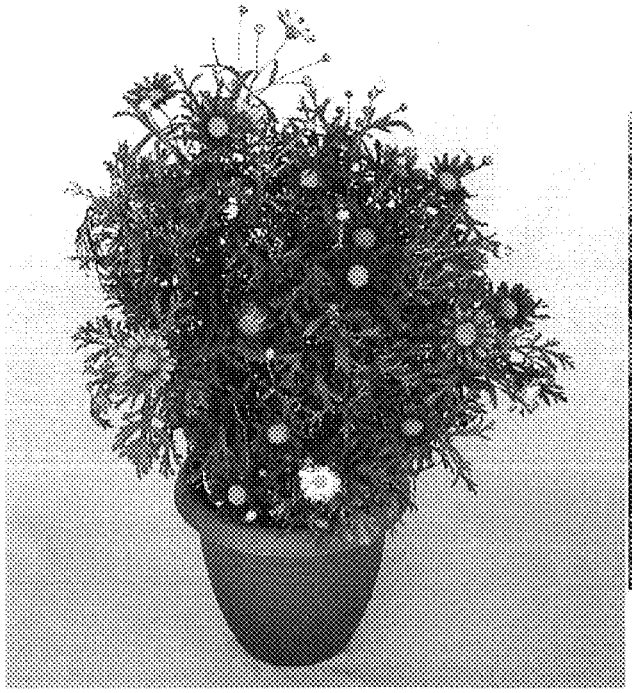
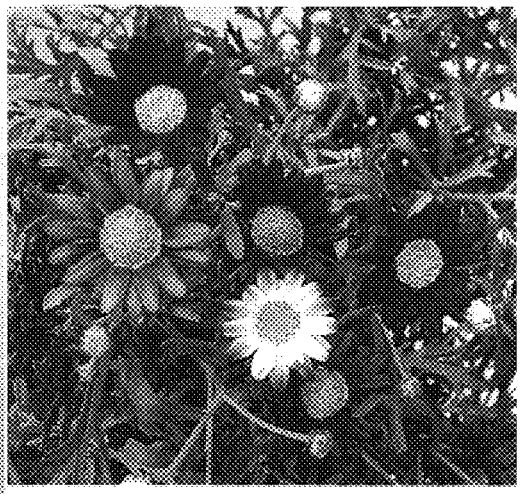

* * * * *